United States Patent [19]

Ross

[11] Patent Number: 4,820,156

[45] Date of Patent: Apr. 11, 1989

[54] TREPHINE DENTAL DRILL

[75] Inventor: Stanley E. Ross, Boca Raton, Fla.

[73] Assignee: Ross Systems Corporation, Palm Beach, Fla.

[21] Appl. No.: 947,176

[22] Filed: Dec. 29, 1986

[51] Int. Cl.$^4$ ............................................... A61C 3/02
[52] U.S. Cl. ................................... 433/165; 433/173; 408/703
[58] Field of Search ............... 433/165, 166, 173, 174; 408/703; 128/310

[56] References Cited

U.S. PATENT DOCUMENTS

| | | | |
|---|---|---|---|
| 2,188,631 | 1/1940 | Kraus | 408/703 |
| 2,525,669 | 10/1950 | Hainault | 128/310 |
| 2,947,206 | 8/1960 | Flanagan | 408/703 |
| 4,021,920 | 5/1977 | Kirschner et al. | 433/165 |
| 4,359,318 | 11/1982 | Gittleman | 433/173 |
| 4,431,416 | 2/1984 | Niznick | 433/174 |
| 4,511,334 | 4/1985 | Grafelmann | 433/165 |

Primary Examiner—John J. Wilson
Attorney, Agent, or Firm—Burns, Doane, Swecker & Mathis

[57] ABSTRACT

A dental trephine drill cuts a bore having a central core. The drill includes a shank having a fluid passage for conducting drilling fluid and a cutting head disposed at a front end of the shank. The cutting head includes front and side faces. The end face surrounds a central hole and includes a plurality of end cutting edges extending from the hole to an outer periphery of the end face. The side face includes a plurality of longitudinal grooves, a longitudinal edge of which defines a side cutting edge. An aperture in each groove communicates the grooves with the interior of the head for conducting drilling fluid into the grooves to cool the drill head and bone tissue.

12 Claims, 2 Drawing Sheets

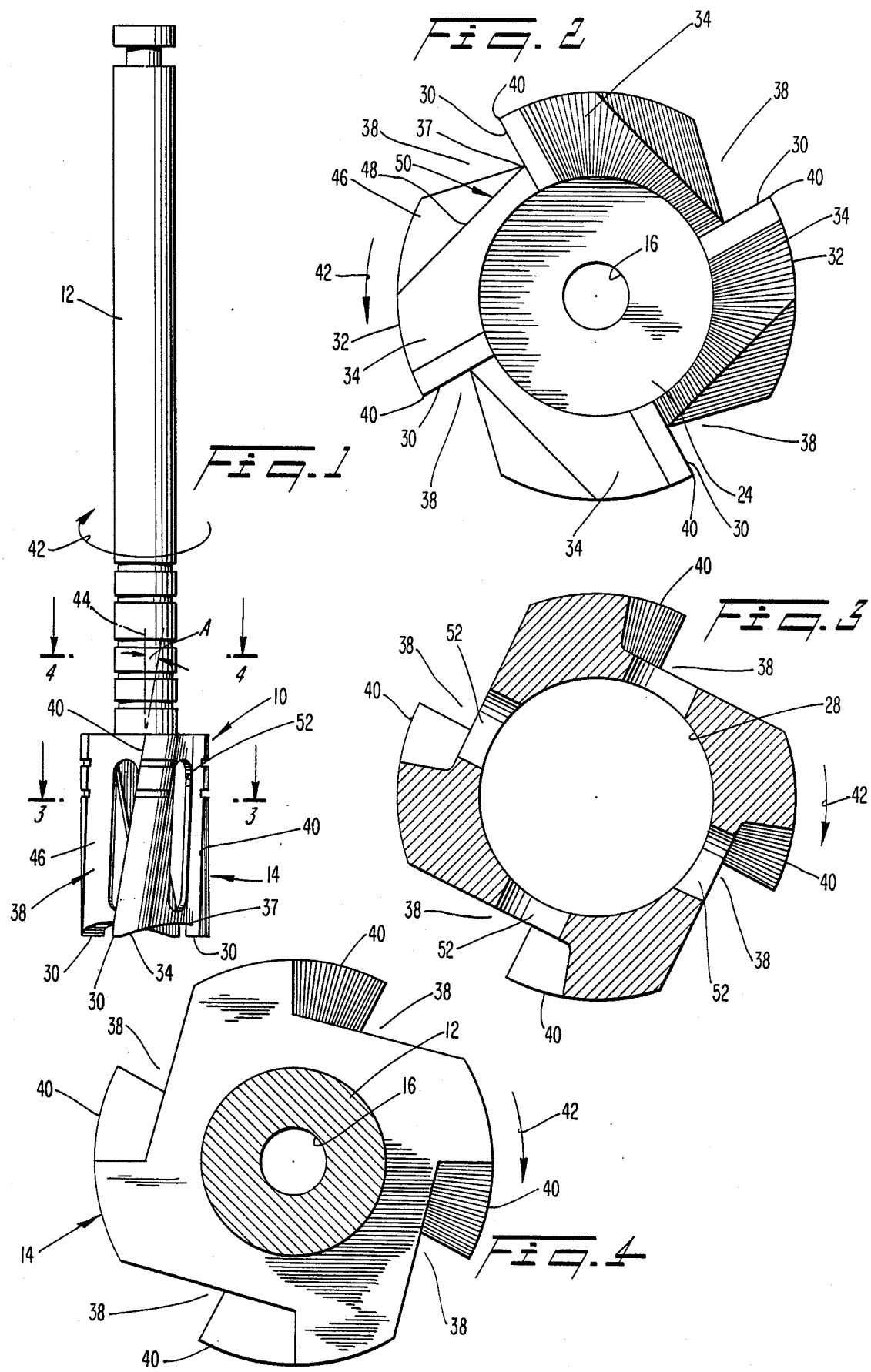

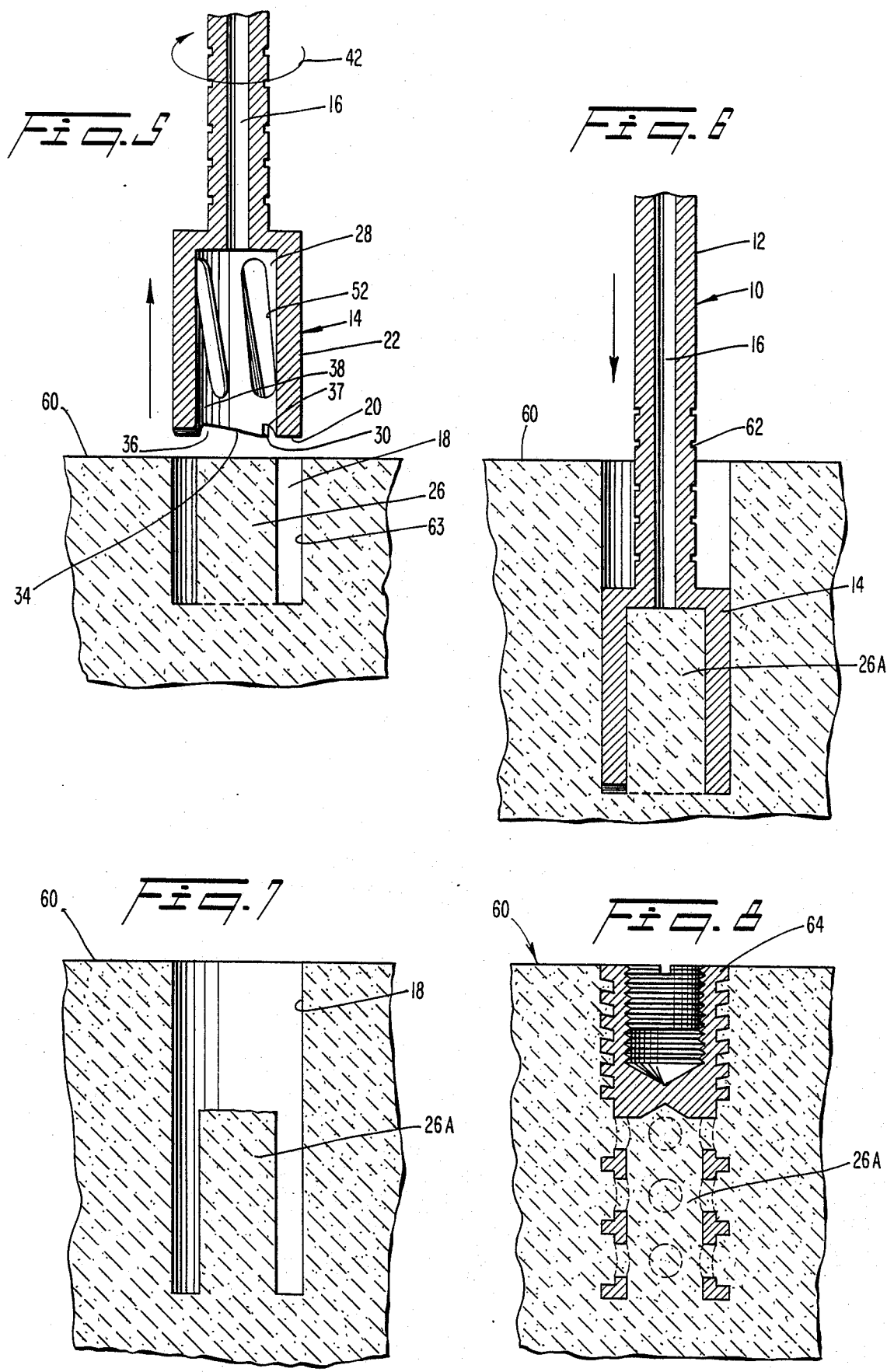

TREPHINE DENTAL DRILL

BACKGROUND OF THE INVENTION

The present invention relates to dental drills and, in particular, to dental trephine drills.

A conventional dental technique for installing a prosthesis involves the installation of an anchor within a bore in the jaw bone, and the subsequent attachment of the prosthesis to the anchor. The bore is drilled by a trephine drill with the intention that a center core will remain at the base of the bore. The front end of the anchor is hollow in order to receive the core in telescoping fashion. The hollow end of the anchor contains throughholes through which the bone tissue can grow to secure the anchor in place.

In some instances the anchor is of the type containing self-tapping screw threads which cut through the bone tissue as the anchor is screwed into the bore. In such instances it is unnecessary for the diameter of the bore to be drilled with precision. However, the act of screwing self-tapping threads through the bone tissue has been determined to impart considerable trauma to the bone tissue, impairing the ability of the bone tissue to regenerate itself.

Also, presently available dental trephine drills do not easily cut through jaw bone tissue; drilling operations conducted with such drills are tedious and time-consuming, adding to the discomfort of the patient.

As described in copending, commonly assigned U.S. patent application Ser. Nos. 896,524, now U.S. Pat. No. 4,744,755 and 896,101, now U.S. Pat. No. 4,744,754 filed together on Aug. 13, 1986, the present inventor has determined that it is unnecessary to utilize self-tapping threads in order to secure an anchor in place. Rather, by drilling a bore having a diameter large enough to accommodate the outer diameter of the anchor, the anchor can be pushed directly into the bore, thereby eliminating the trauma to the bone caused by the screwing-in of self-tapping threads. However, conventional dental trephine drills have not produced satisfactory bores to enable the anchors to be conveniently pushed in place. Rather, the outer wall of the bore contains burrs which resist entry of the anchor. To remove the burrs, it has been necessary to repeatedly reciprocate the drill within the bore. Such a practice is time-consuming, increases the discomfort of the patient and may result in the bore being made of larger diameter than is desired for optimal results. That is, as noted in the above-referenced copending patent applications, it is desirable to enable the outer surface of the anchor to contact the wall of the bore in order to promote the occurrence of blood clotting and the retention of blood clots in the vicinity of the entire wall of the bore so that the regeneration of the bone tissue is accelerated. The attainment of this goal can be impaired if the bore diameter is excessively enlarged as the result of repeated reciprocation of the drill when the bore is being drilled.

Another concern during the drilling of bores in bone tissue relates to the fact that the bone tissue can be damaged by high temperature build-ups occurring as the result of frictional contact with the drill. Such temperature-induced damage can adversely affect the ability of the bone tissue to regenerate itself and grow against the anchor. Conventional trephine drills include a central passage for conducting fluid such as a saline solution or sterile water to the drill head intended for cooling the bone tissue and the drill head as well as flushing cuttings from the bore. However, as the bone core enters the front opening of the drill head, the flow of fluid is obstructed, whereby the benefits which would be otherwise attributable to the fluid flow are minimized. Also, such blockage of fluid flow creates a fluid pressure build-up which resists the advancement of the drill head.

SUMMARY OF THE INVENTION

The present invention relates to a dental trephine drill of the type which cuts a bore having a central bore. The drill comprises a shank having a fluid passage extending longitudinally therethrough for conducting drilling fluid. A cutting head is disposed at a front end of the shank. The head is hollow and includes a front end face and a side face extending longitudinally rearwardly from an outer periphery of the end face. The end face surrounds a central hole adapted to receive a core formed in bone tissue being cut. A plurality of end cutting edges is disposed on the end face and extends from the hole to the outer periphery of the end face. The side face includes a plurality of longitudinally oriented grooves extending rearwardly from the end face. A circumferentially trailing edge of each groove defines a longitudinally extending side cutting edge at least a substantial portion of which is spaced at a constant distance from a rotary axis of the drill so as to cut a longitudinal bore. An aperture is disposed in each groove for communicating the grooves with the interior of the head in order to conduct drilling fluid into the grooves to flush and cool the side cutting edges.

Preferably, radially outer ends of the end cutting edges intersect longitudinal front ends of respective ones of the side cutting edges. The end face is relieved longitudinally rearwardly and radially inwardly in front of each end cutting edge to conduct drilling fluid from the grooves to the end cutting edges to cool and flush the latter.

Preferably, each aperture extends longitudinally along each groove, each aperture preferably being in the form of a longitudinally elongate slot.

Preferably, the side edges are each raked at an acute angle relative to the central rotary axis, such angle preferably being in the range of from 5 to 15 degrees and most preferably is about 10 degrees.

BRIEF DESCRIPTION OF THE DRAWINGS

The objects and advantages of the invention will become apparent from the following detailed description of a preferred embodiment thereof in connection with the accompanying drawings, in which like numerals designate like elements, and in which:

FIG. 1 is a side elevational view of a dental trephine drill according to the present invention;

FIG. 2 is a front end view of the trephine drill;

FIG. 3 is a cross-sectional view taken along the line 3—3 in FIG. 1;

FIG. 4 is a cross-sectional view taken along the line 4—4 in FIG. 1;

FIG. 5 is a longitudinal sectional view taken through the drill after the drill has cut an initial bore in bone tissue;

FIG. 6 is similar to FIG. 5 after the initially formed core has been removed and the drill has been further advanced to extend the bore;

FIG. 7 is a longitudinal sectional view through the bore after the drill has been removed; and FIG. 8 is a longitudinal sectional view taken through the bore and through an anchor which has been inserted into the bore, after the bone tissue has grown against the anchor.

DETAILED DESCRIPTION OF A PREFERRED EMBODIMENT OF THE INVENTION

A dental trephine drill 10 according to the present invention includes a mounting shank 12 and a cutting head 14 disposed at a longitudinal front end of the shank. A longitudinal fluid passage 16 extends through the shank for conducting flushing fluid such as a saline solution or sterile water for flushing cuttings from a bore 18 cut by the drill.

The head 14 is hollow and includes a front end face 20 and a side face 22 extending longitudinally rearwardly from the end face 20. The end face surrounds a center hole 24 which is adapted to receive a core 26 formed during the cutting of a bore (FIG. 5). The fluid passage 16 communicates with the interior 28 of the head 14 and thus with the hole 24.

Formed in the end face 20 is a plurality of first cutting edges 30 extending radially outwardly from the hole 24 to an outer periphery 32 of the front face 20.

Surface portions 34 of the front face 20 disposed circumferentially behind the end cutting edges 30 extend longitudinally rearwardly from the end cutting edges (see FIGS. 1 and 5) to define radial openings 36 which accommodate a flow of drilling fluid. A circumferentially rear end of each such surface portion 34 terminates adjacent the next end cutting edge 30 at a location 37 spaced slightly longitudinally rearwardly and radially inwardly of such end cutting edge to define a relief which accommodates the flow of drilling fluid.

Formed in the cylindrical side face 22 are a plurality of longitudinally oriented grooves 38 which extend longitudinally rearwardly from the end face 20. Each groove 38 includes a longitudinally extending edge 40 which defines a side cutting edge. That side cutting edge 40 constitutes a trailing edge of the respective groove 38 with reference to the direction of rotation 42 of the drill.

The grooves 38 and associated side cutting edges 40 preferably extend at an acute angle A of from 5° to 15° (preferably about 10°) relative to the longitudinal axis of rotation 44 (i.e., the edges 40 are raked rearwardly). All points on the side cutting edge 40 are spaced radially equidistantly from the axis 44, so that the side edges 40 cut a cylindrical bore.

The end cutting edges 30 intersect and extend radially inwardly from longitudinal front ends of respective side cutting edges 40. As can be seen in FIG. 2, the floor 46 of each groove 38 intersects the end face 20 along a line 48 which extends from the outer periphery 34 of the end face to the location 37, which location 37 is situated radially inwardly from the outer periphery 34. It will be appreciated that each line 48 constitutes an outer edge of a respective surface portion 34 of the end face 20.

The above-described configuration of the grooves 38 result in the formation of longitudinal passages or reliefs 50 (FIG. 2) which communicate the grooves with the end face 20 to accommodate the flow of drilling fluid therebetween.

The floor 46 is not planar, but rather is slightly curved so as to be visible in a front end view (FIG. 2).

Extending through the floor 46 of each groove is an aperture 52 which communicates each groove with the interior 28 of the head 14. Thus, drilling fluid can be conducted radially outwardly from that interior 28 to the grooves 38 in order to cool the drill and bone and flush cuttings from the grooves 38, as well as prevent fluid pressure build-ups. The apertures 52 are arranged to extend in a longitudinal direction. That is, the apertures may be of longitudinally elongate slot shape as depicted, or each aperture could comprise a series of small longitudinally spaced holes. Such a longitudinally extending configuration ensures that drilling fluid can enter the grooves through the apertures, even as a bone core is being progressively received in the cylindrical interior of the head 14. Also, such fluid cools the drill head and the bone tissue of the bore wall.

IN OPERATION, the drill head 14 is advanced into a jaw bone 60 of a patient. The end cutting edges 30 cut an annular kerf or bore 18 in the bone, leaving a center core of bone 26. Pressurized drilling fluid (e.g., saline solution or sterile water) flows through the front hole 24 of the drill head to clean and cool the cutting edges and flush cuttings from the bore. The outer wall 63 of the bore is cut by the side cutting edges 40. Drilling fluid flows radially outwardly through the apertures 52 into the grooves 38 to clean and cool the side edges 40 and flush cuttings from the bore.

Eventually, as the core 26 enters the front hole 24 of the head, the flow of drilling fluid through the hole 24 is seriously restricted. However, the flow of drilling fluid through the apertures 52 prevents excessive hydraulic pressure build-ups within the drill. Also, such fluid cools the drill head and the bone tissue of the bore wall.

Furthermore, since the grooves 38 communicate with the end face 20 and with the end cutting edges 30 thereon, via passages 50, fluid is able to flow longitudinally forwardly to clean and cool the end cutting edges 30 to compensate for a lack of fluid from the hole 24.

Since the apertures 52 extend longitudinally along the grooves 38, the pressurized fluid continues to be discharged therethrough, even as the apertures 52 become progressively blocked by the core 26. The fluid is also able to contact the outer wall of the bone core via the apertures 52 to cool such bone core.

After an initial portion of the bore has been formed (FIG. 5), the core 26 is intentionally broken off and the drill is reinserted into the bore 18 to extend the bore 18 (FIG. 6) and form a new core 26A. The depth of the bore 18 can be monitored by viewing indicator slits 62 formed in the outer periphery of the stem 12 and head 14. Alternatively, a stop can be employed as disclosed in the present inventor's copending U.S. patent application Ser. No. 934,638 filed Nov. 25, 1986.

After the bore 18 has been completed, an anchor 64 is pushed into the bore, as described in copending U.S. Ser. Nos. 920,781, now U.S. Pat. No. 4,744,753 and 896,101 wherein the core 26A enters a front opening in the anchor. Eventually, bone tissue grows against the anchor and through holes therein to permanently secure the anchor in place. The anchor is adapted to receive a prosthesis (not shown) as described in copending U.S. patent application Ser. Nos. 920,796, now U.S. Pat. No. 4,744,756 and 920,781.

The drill is preferably formed of corrosive resistant, heat treated, stainless steel No. 420, although other materials may be suitable. Drills of different outer diameter are provided for forming bores of different size to accommodate an appropriate anchor. For example, drills forming bores having a diameter in the range of from 3.5 mm to 5.5 mm are provided.

A dental trephine drill according to the present invention enables a bore and core to be formed quickly and with minimal trauma to the bone and minimal discomfort to the patient. The side cutting edges assure that the outer wall of the bore is cut cleanly without burrs. Thus, it is unnecessary to repeatedly reciprocate the drill within the bore to remove burrs. This results in a shorter drilling period and a more accurately dimensioned bore which assures that a proper fit with the anchor will occur.

The presence of apertures in the grooves prevents the creation of hydraulic pressure build-ups which could resist advancement of the drill. Since the apertures extend longitudinally, this pressure relief continues even as the apertures are progressively blocked by the core. The fluid flowing through the apertures cleans and cools the side cutting edges and flushes cuttings from the bore. The fluid is able to travel longitudinally forwardly from the grooves to clean and cool the end cutting edges, since the front ends of the grooves communicate with the area located in front of the end cutting edges. Also, such fluid cools the bone, i.e., the inner wall of the bore and the outer wall of the bone core to minimize the occurrence of thermal damage thereto.

Although the present invention has been described in connection with a preferred embodiment thereof, it will be appreciated by those skilled in the art that additions, modifications, substitutions and deletions not specifically described may be made without departing from the spirit and scope of the invention as defined in the appended claims.

I claim:

1. A dental trephine drill of the type which cuts a bore having a central core, said drill comprising a shank having a fluid passage extending longitudinally therethrough for conducting drilling fluid, a cutting head disposed at a front end of said shank, said head being hollow to form an interior portion communicating with said passage for receiving drilling fluid, said head including a front end face and a side face extending longitudinally rearwardly from an outer periphery of said end face, said end face surrounding a central hole adapted to receive a core formed in bone tissue being cut, a plurality of end cutting edges disposed on said end face and extending from said hole to said outer periphery of said end face, said side face including a plurality of longitudinally oriented grooves extending rearwardly from said end face, a circumferentially trailing edge of each groove defining a longitudinally extending side cutting edge at least a substantial portion of which being spaced at a constant distance from a rotary axis of said drill so as to cut a cylindrical bore, aperture means in each groove communicating said grooves with the interior portion of said head for conducting drilling fluid from the interior portion into said grooves to cool and flush said side cutting edges and relieve fluid pressure within the interior portion.

2. A trephine drill according to claim 1, wherein radially outer ends of said end cutting edges intersect longitudinally front ends of respective ones of said side cutting edges.

3. A trephine drill according to claim 2, wherein said end face is relieved longitudinally rearwardly and radially inwardly in front of each end cutting edge to conduct drilling fluid from said grooves to said end cutting edges to cool and flush the latter.

4. A trephine drill according to claim 3, wherein the portions of said end face disposed between a pair of successive end cutting edges are inclined longitudinally rearwardly from a leading one of said pair to a location in front of and longitudinally rearwardly of a trailing one of said pair.

5. A trephine drill according to claim 1, wherein each said aperture means extends longitudinally along each said groove.

6. A trephine drill according to claim 1, wherein each said aperture means comprises a longitudinally elongate slot.

7. A trephine drill according to claim 6, wherein said side edges are raked by an angle in the range of from 5 to 15 degrees.

8. A trephine drill according to claim 1, wherein said side edges are each raked at an acute angle relative to the central rotary axis.

9. A trephine drill according to claim 7, wherein said angle is substantially 10 degrees.

10. A trephine drill according to claim 1, wherein said interior portion is of circular cross-section with a constant diameter along its longitudinal extent.

11. A dental trephine drill of the type which cuts a bore having a central core, said drill comprising a shank having a fluid passage extending longitudinally therethrough for conducting drilling fluid, a cutting head disposed at a front end of said shank, said head being hollow to form an interior portion communicating with said passage for receiving drilling fluid, said head including a front face and a side face extending longitudinally rearwardly from an outer periphery of said end face, said end face surrounding a central hole adapted to receive a core formed in bone tissue being cut, a plurality of end cutting edges disposed on said end face and extending from said hole to said outer periphery of said end face, said side face including a plurality of longitudinally oriented grooves extending rearwardly from said end face, a circumferentially trailing edge of each groove defining a longitudinal side cutting edge at least a substantial portion of which being spaced at a constant distance from a rotary axis of said drill so as to cut a cylindrical bore, aperture means extending longitudinally along each said groove for communicating said grooves with the interior portion of said head for conducting drilling fluid from the interior portion into said grooves to cool and flush said side cutting edges and relieve fluid pressure within the interior portion, said side cutting edges being raked at an acute angle relative to a rotary axis of said drill, longitudinal front ends of said side cutting edges intersecting radially outer ends of respective ones of said end cutting edges, said end faces being relieved longitudinally rearwardly and radially inwardly circumferentially in front of each end cutting edge to conduct drilling fluid from said groove to said end cutting edges to cool and flush the latter.

12. A trephine drill according to claim 11, wherein said interior portion is of circular cross-section with a constant diameter along its longitudinal extent.

* * * * *